(12) United States Patent
Hausen

(10) Patent No.: US 8,397,973 B1
(45) Date of Patent: Mar. 19, 2013

(54) WIDE HANDLE FOR TRUE MULTI-FIRE SURGICAL STAPLER

(75) Inventor: Bernard A. Hausen, Redwood City, CA (US)

(73) Assignee: Cardica, Inc., Redwood City, CA (US)

( * ) Notice: Subject to any disclaimer, the term of this patent is extended or adjusted under 35 U.S.C. 154(b) by 315 days.

(21) Appl. No.: 12/716,034

(22) Filed: Mar. 2, 2010

Related U.S. Application Data

(60) Provisional application No. 61/209,692, filed on Mar. 9, 2009.

(51) Int. Cl.
*A61B 17/064* (2006.01)

(52) U.S. Cl. .............. 227/176.1; 227/175.1; 227/120; 227/135; 227/136; 227/19

(58) Field of Classification Search .............. 227/175.1, 227/176.1, 120, 135–136, 19
See application file for complete search history.

(56) References Cited

U.S. PATENT DOCUMENTS

| | | |
|---|---|---|
| 3,581,551 A | 6/1971 | Wilkinson |
| 3,650,453 A | 3/1972 | Smith, Jr. |
| 3,675,688 A | 7/1972 | Bryan et al. |
| 3,837,555 A * | 9/1974 | Green ........................ 227/130 |
| 3,899,914 A | 8/1975 | Akiyama |
| 3,955,581 A | 5/1976 | Spasiano et al. |
| 4,086,926 A | 5/1978 | Green et al. |
| 4,228,895 A | 10/1980 | Larkin |
| 4,275,813 A | 6/1981 | Noiles |
| 4,475,679 A | 10/1984 | Fleury, Jr. |
| 4,633,861 A | 1/1987 | Chow et al. |
| 4,655,222 A | 4/1987 | Florez et al. |
| 4,719,917 A | 1/1988 | Barrows et al. |
| 4,762,260 A | 8/1988 | Richards et al. |
| 4,969,591 A | 11/1990 | Richards et al. |
| 4,978,049 A | 12/1990 | Green |
| 5,156,315 A | 10/1992 | Green et al. |
| 5,170,925 A | 12/1992 | Madden et al. |

(Continued)

FOREIGN PATENT DOCUMENTS

| | | |
|---|---|---|
| EP | 1238634 | 9/1994 |
| EP | 1464287 | 10/2004 |

(Continued)

OTHER PUBLICATIONS

Gong, Shao W., "Perfectly flexible mechanism and integrated mechanism system design", *Mechanism and Machine Theory 39* (2004), (Nov. 2004),1155-1174.

(Continued)

*Primary Examiner* — Brian D Nash
*Assistant Examiner* — Michelle Lopez
(74) *Attorney, Agent, or Firm* — Cardica, Inc.

(57) ABSTRACT

A surgical apparatus may include at least one feeder belt; a plurality of staples frangibly affixed to each feeder belt, where each staple includes two ends, a first end frangibly connected to a corresponding feeder belt and a second, free end; and a handle within which at least part of at least one feeder belt is received, where that feeder belt extends along a path within that handle that is at least partially nonlinear. A method for operating a surgical apparatus, including providing a surgical stapler including an end effector, a shaft, a handle and at least one feeder belt, where staples are frangibly affixed to each feeder belt; deploying a plurality of staples from the end effector; and advancing at least one feeder belt along a nonlinear path after deploying the staples, whereby fresh staples are moved into the end effector into position for deployment.

15 Claims, 1 Drawing Sheet

U.S. PATENT DOCUMENTS

| | | |
|---|---|---|
| 5,192,288 A | 3/1993 | Thompson et al. |
| 5,307,976 A | 5/1994 | Olson et al. |
| 5,413,272 A | 5/1995 | Green et al. |
| 5,476,206 A | 12/1995 | Green |
| 5,547,117 A | 8/1996 | Hamblin et al. |
| 5,553,765 A | 9/1996 | Knodel et al. |
| 5,620,289 A | 4/1997 | Curry |
| 5,630,541 A | 5/1997 | Williamson, IV et al. |
| 5,655,698 A | 8/1997 | Yoon |
| 5,662,260 A | 9/1997 | Yoon |
| 5,692,668 A | 12/1997 | Schulze et al. |
| 5,810,855 A | 9/1998 | Rayburn et al. |
| 5,816,471 A | 10/1998 | Plyley et al. |
| 5,855,311 A | 1/1999 | Hamblin et al. |
| 5,871,135 A | 2/1999 | Williamson, IV et al. |
| 5,875,538 A | 3/1999 | Kish et al. |
| 5,894,979 A | 4/1999 | Powell |
| 5,918,791 A | 7/1999 | Sorrentino et al. |
| 5,964,774 A | 10/1999 | McKean et al. |
| 6,306,149 B1 | 10/2001 | Meade |
| 6,419,682 B1 | 7/2002 | Appleby et al. |
| 6,592,597 B2 | 7/2003 | Grant et al. |
| 6,602,252 B2 | 8/2003 | Mollenauer |
| 6,716,232 B1 | 4/2004 | Vidal et al. |
| 6,817,508 B1 | 11/2004 | Racenet |
| 6,843,403 B2 | 1/2005 | Whitman |
| 7,025,747 B2 | 4/2006 | Smith |
| 7,055,730 B2 | 6/2006 | Ehrenfels et al. |
| 7,097,089 B2 | 8/2006 | Marczyk |
| 7,111,768 B2 | 9/2006 | Cummins et al. |
| 7,128,253 B2 | 10/2006 | Mastri et al. |
| 7,140,527 B2 | 11/2006 | Ehrenfels et al. |
| 7,168,604 B2 | 1/2007 | Milliman et al. |
| 7,172,104 B2 | 2/2007 | Scirica et al. |
| 7,179,267 B2 | 2/2007 | Nolan et al. |
| 7,207,471 B2 | 4/2007 | Heinrich et al. |
| 7,213,736 B2 | 5/2007 | Wales et al. |
| 7,225,963 B2 | 6/2007 | Scirica |
| 7,225,964 B2 | 6/2007 | Mastri et al. |
| 7,234,624 B2 | 6/2007 | Gresham et al. |
| 7,238,195 B2 | 7/2007 | Viola |
| 7,258,262 B2 | 8/2007 | Mastri et al. |
| 7,401,720 B1 | 7/2008 | Durrani |
| 7,434,715 B2 | 10/2008 | Shelton, IV et al. |
| 7,467,740 B2 | 12/2008 | Shelton, IV et al. |
| 7,497,865 B2 | 3/2009 | Willis et al. |
| 7,506,791 B2 | 3/2009 | Omaits et al. |
| 7,517,356 B2 | 4/2009 | Heinrich |
| 7,588,177 B2 | 9/2009 | Racenet |
| 7,604,151 B2 | 10/2009 | Hess et al. |
| 7,635,073 B2 | 12/2009 | Heinrich |
| 7,635,373 B2 | 12/2009 | Ortiz |
| 7,641,432 B2 | 1/2010 | Lat et al. |
| 7,644,848 B2 | 1/2010 | Swayze et al. |
| 2003/0120284 A1 | 6/2003 | Palacios et al. |
| 2003/0236551 A1 | 12/2003 | Peterson |
| 2005/0184121 A1 | 8/2005 | Heinrich |
| 2006/0011699 A1 | 1/2006 | Olson et al. |
| 2006/0041273 A1 | 2/2006 | Ortiz et al. |
| 2006/0151567 A1 | 7/2006 | Roy |
| 2006/0253143 A1 | 11/2006 | Edoga et al. |
| 2007/0027472 A1 | 2/2007 | Hiles et al. |
| 2007/0034668 A1 | 2/2007 | Holsten et al. |
| 2007/0073341 A1 | 3/2007 | Smith et al. |
| 2007/0083234 A1 | 4/2007 | Shelton, IV et al. |
| 2007/0118163 A1 | 5/2007 | Boudreaux et al. |
| 2007/0125828 A1 | 6/2007 | Rethy et al. |
| 2007/0175950 A1 | 8/2007 | Shelton, IV et al. |
| 2008/0078807 A1 | 4/2008 | Hess et al. |
| 2008/0272175 A1 | 11/2008 | Holsten et al. |

FOREIGN PATENT DOCUMENTS

| | | |
|---|---|---|
| EP | 1736104 | 3/2009 |
| JP | 2005160933 | 6/2005 |
| RU | 2080833 | 6/1997 |
| WO | WO-81/01953 | 7/1981 |
| WO | WO-85/01427 | 4/1985 |

OTHER PUBLICATIONS

Lim, Jonas J., et al., "A review of mechanism used in laparascopic surgical instruments", *Mechanism and Machine Theory 38*, (2003),1133-1147.

Lim, Jyue B., "Type Synthesis of a Complex Surgical Device", *Masters Thesis*, (Feb. 21, 2001).

Lim, Jonas J., et al., "Application of Type Synthesis Theory to the Redesign of a Complex Surgical Instrument", *Journal of Biomechanical Engineering* (124), (Jun. 2004),265-272.

Kolios, Efrossini et al., "Microlaparoscopy", *J. Endourology 18*(9), (Nov. 2004),811-817.

Steichen, Felicien M., et al., "Mechanical Sutures in Surgery", *Brit. J. Surg. 60*(3), (Mar. 1973),191-197.

"Notification of Transmittal of the International Search Report and the Written Opinion of the International Searching Authority", PCT/US2008/075449.

"International Search Report", PCT/US2008/075449.

"Written Opinion of the International Searching Authority", PCT/US2008/075449.

\* cited by examiner

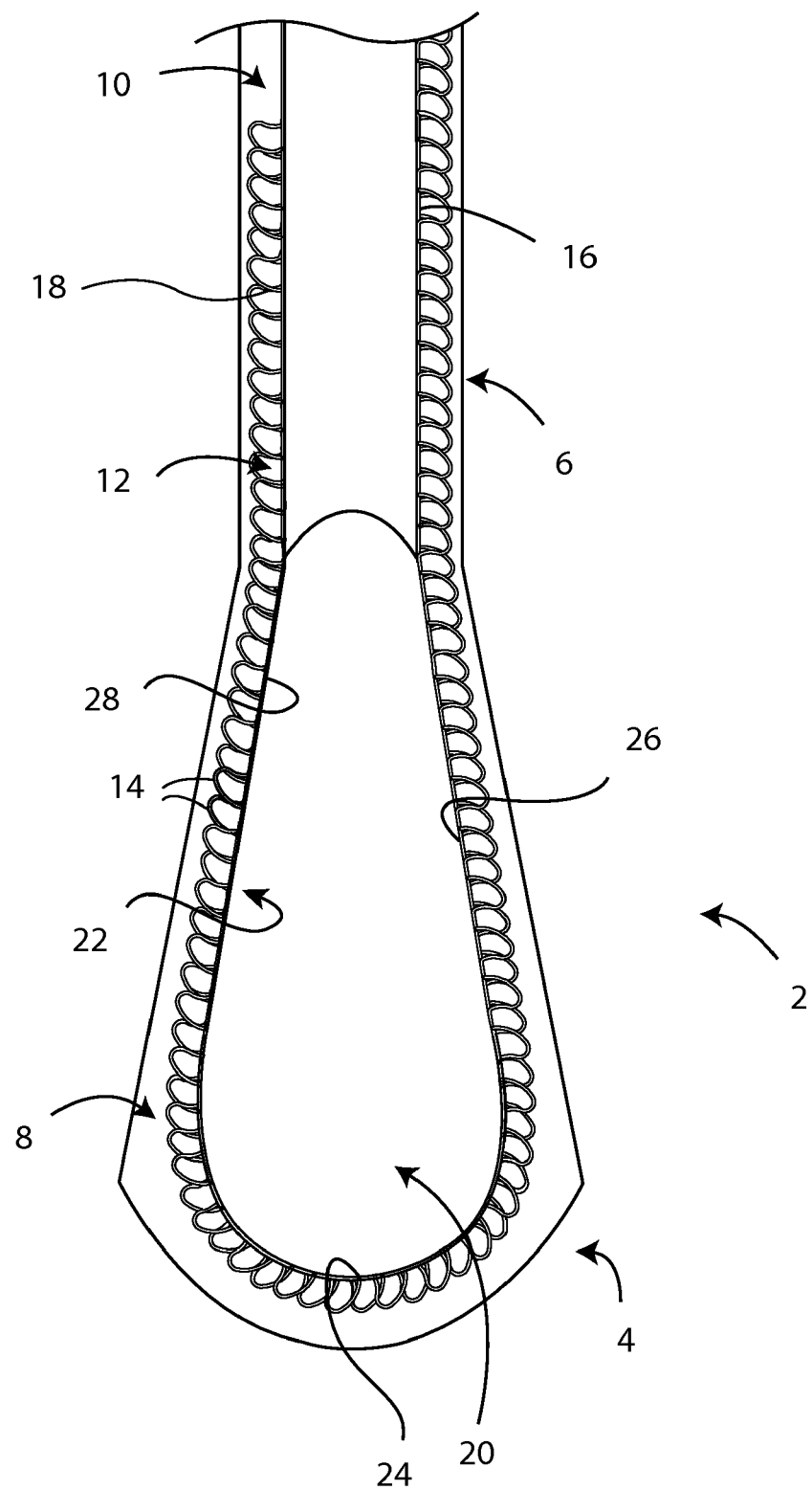

WIDE HANDLE FOR TRUE MULTI-FIRE SURGICAL STAPLER

This application claims priority to U.S. Provisional Patent Application Ser. No. 61/209,692, filed on Mar. 9, 2009, which is herein incorporated by reference in its entirety.

FIELD OF THE INVENTION

The invention generally relates to surgical instruments, and more specifically to surgical staplers.

BACKGROUND

An endocutter is a surgical tool that staples and cuts tissue to transect that tissue while leaving the cut ends hemostatic. An endocutter is small enough in diameter for use in minimally invasive surgery, where access to a surgical site is obtained through a trocar, port, or small incision in the body. An exemplary endocutter, with true multi-fire capability, is the MICROCUTTER™ brand endocutter proposed by Cardica, Inc. of Redwood City. That device is described in, for example, U.S. patent application Ser. No. 11/851,379, filed on Sep. 6, 2007, published as U.S. Patent Application Publication No. 2009/0065552 on Mar. 12, 2009 (the "Endocutter Application"), which is herein incorporated by reference in its entirety. The MICROCUTTER™ brand endocutter achieves true multi-fire capability through staple-on-a-strip technology, where staples are frangibly fixed to a feeder belt and sheared from the feeder belt during deployment, after which the feeder belt is advanced to place another set of staples in firing position. Each feeder belt may be slid about a nose located distally within the staple holder, where the nose may be a curved surface or pulley. In this way, two sections of the feeder belt may be generally parallel to one another and spaced apart from one another substantially the same distance as the diameter of the nose, to facilitate motion of the feeder belt through the staple holder and/or through a shaft connected to the staple holder.

BRIEF DESCRIPTION OF THE DRAWINGS

FIG. 1 is a side schematic view of a handle of a surgical stapler.

DETAILED DESCRIPTION

Referring to FIG. 1, a surgical stapler 2 may include a handle 4 and a shaft 6 attached to the distal end of the handle 4, or to any other suitable part of the handle 4. The handle 4 is advantageously at least partially hollow, defining a plenum 8 within, and the shaft 6 is advantageously tubular, with a lumen 10 defined therein. Alternately, the handle 4 and shaft 6 may be shaped in any other suitable manner. The surgical stapler 2 may also include an end effector that includes a staple holder and anvil, as set forth in the Endocutter Application.

A feeder belt 12 may be received within the handle 4 and/or the shaft 6, where staples 14 are frangibly connected to the feeder belt 12. The feeder belt 12 and staples 14 may be substantially as set forth in the Endocutter Application. The feeder belt 12 may extend from the plenum 8 within the handle 4 into the lumen 10 of the shaft 6, and from there into the staple holder. The feeder belt 12 may be a continuous loop that wraps around a nose in the staple holder, as described in the Endocutter Application, then extends back through the lumen 10 of the shaft 6 into the plenum 8 within the handle 4. Alternately, the feeder belt 12 need not be continuous, and may have two discrete ends that are not connected to one another. Where the feeder belt 12 extends in both directions through the lumen 10 of the shaft 6, the feeder belt 12 may be considered to have two segments 16, 18, where those segments 16, 18 may be spaced apart from one another in the lumen 10 of the shaft 6. Advantageously, the segments 16, 18 may be substantially parallel to one another within the lumen 10 of the shaft 6 along the length of the shaft 6. Alternately, the segments 16, 18 may be oriented differently with regard to one another along at least part of the length of the shaft 6. The segments 16, 18 are not specific, discrete sections of the feeder belt 12; the portions of the feeder belt 12 that may be considered the segments 16, 18 change as the feeder belt 12 is advanced, as described in greater detail below.

Within the plenum 8 in the handle 4, the segments 16, 18 may diverge, such that the segments 16, 18 are not parallel. A mandrel 20 may be positioned within the plenum 8 in the handle 4. such that the feeder belt 12 engages at least part of the surface 22 of the mandrel 20. In this way, at least part of the surface 22 of the mandrel 20 defines a path within the handle 4 along which the feeder belt 12 extends, and along which the feeder belt 12 is slidable. That is, the feeder belt 12 wraps around at least part of the surface 22 of the mandrel 20. The mandrel 20 may have any suitable shape. As one example, the proximal surface 24 of the mandrel 20 may be a convex curve. As another example, the mandrel 20 may also, or instead, include two surfaces 26, 28 that form a nonzero angle relative to one another. Those surfaces 26, 28 may be located distal to the proximal surface 24 of the mandrel, and those surfaces 26, 28 may form an acute angle relative to one another. Alternately, the surface 26, 28 may be nonparallel to one another in a different manner; for example, at least one surface 26, 28 may be curved. The surfaces 26, 28 may be spaced apart from one another, or may contact one another. Alternately, the surface 22 of the mandrel 20 may be configured in any other suitable manner. The mandrel 20 may be wider than the diameter of the shaft 6, such that the path along which the feeder belt 12 travels is wider than the diameter of the shaft 6. The mandrel 20 defines a nonlinear path along which the feeder belt 12 extends in order to allow the placement of more staples within the handle 4 than would be possible if the feeder belt 12 merely extended linearly within the handle, thereby allowing more actuations of the surgical stapler 2. Further, the mandrel 20 allows the feeder belt 12 to be a continuous loop, such that unfired staples on the feeder belt 12, prior to the first actuation of the surgical stapler 2, may extend proximally from the distal end of the shaft 6, along the nonlinear mandrel 20, then distally to the distal end of the shaft 6, maximizing the number of times the surgical stapler 2 can be actuated.

The surgical stapler 2 may be actuated substantially as set forth in the Endocutter Application, with the differences set forth herein. A plurality of staples 14 are deformed and then frangibly separated from the feeder belt 12, at the staple holder. The feeder belt 12 is then advanced through the lumen 10 of the shaft 6, to bring a new set of unfired staples 14 into the staple holder. As the feeder belt 12 is advanced, at least part of the feeder belt 12 slides or otherwise travels along a nonlinear path. For example, motion of the feeder belt 12 along the nonlinear surface 22 of the mandrel 20 results in advancement of the feeder belt 12 along a nonlinear path. The feeder belt 12 may be advanced such that the lower segment 18 of the feeder belt 12 moves proximally into the plenum 8 within the handle 4, moves away from the longitudinal centerline of the shaft 6 along a lower surface 28 of the mandrel 20, moves along the curved proximal surface 24 of the mandrel 20, then moves distally along an upper surface 26 of the mandrel 20 and distally into the lumen 10 of the shaft 6. Alternately, the feeder belt 12 may move in the opposite direction. In either direction, one segment of the feeder belt 12 moving proximally out of the lumen 10 of the shaft 6 moves away from the segment of the feeder belt 12 moving distally into the lumen 10 of the shaft 6. Further, in either direction, one segment of the feeder belt 12 moving distally into the lumen 10 of the shaft 6 moves toward the segment of the feeder belt 12 moving proximally out of the lumen 10 of the shaft 6. The staples 14 are oriented away from the mandrel 20 such that travel of the feeder belt 12 along the mandrel 20 does not deform the staples 14. Once the feeder belt 12 has moved such that fresh, unfired staples 14 are present in the staple holder, the surgical stapler 2 may be actuated again, without the need for replacement of a cartridge or disposable loading unit.

While the invention has been described in detail, it will be apparent to one skilled in the art that various changes and modifications can be made and equivalents employed, without departing from the present invention. It is to be understood that the invention is not limited to the details of construction, the arrangements of components, and/or the method set forth in the above description or illustrated in the drawings. Statements in the abstract of this document, and any summary statements in this document, are merely exemplary; they are not, and cannot be interpreted as, limiting the scope of the claims. Further, the figures are merely exemplary and not limiting. Topical headings and subheadings are for the convenience of the reader only. They should not and cannot be construed to have any substantive significance, meaning or interpretation, and should not and cannot be deemed to indicate that all of the information relating to any particular topic is to be found under or limited to any particular heading or subheading. Therefore, the invention is not to be restricted or limited except in accordance with the following claims and their legal equivalents.

What is claimed is:

1. A surgical apparatus, comprising:
   at least one feeder belt;
   a plurality of staples frangibly affixed to each said feeder belt, wherein each said staple includes two ends, a first end frangibly connected to a corresponding said feeder belt and a second, free end; and
   a handle within which at least part of at least one said feeder belt is received, wherein said feeder belt extends along a path within said handle that is nonlinear at least in part, and wherein at least part of said path moves away from a longitudinal axis of the handle.

2. The apparatus of claim 1, wherein said path includes at least a first segment and a second segment, wherein said first segment and said second segment are nonparallel to one another.

3. The apparatus of claim 2, wherein said path includes at least a first segment and a second segment, wherein said first segment forms a nonzero angle with said second segment.

4. The apparatus of claim 2, wherein said first segment and said second segment are spaced apart from one another in the direction of the length of the path.

5. The apparatus of claim 1, wherein at least one said feeder belt is slidable along said path.

6. The apparatus of claim 1, further comprising a mandrel located within said handle, said mandrel including a surface, wherein at least part of at least one said feeder belt wraps around at least part of said surface of said mandrel, such that said surface of said mandrel defines at least part of said path.

7. The apparatus of claim 6, wherein said mandrel includes a convex proximal surface.

8. The apparatus of claim 7, wherein said mandrel includes two surfaces angled relative to one another at a location distal to said convex proximal surface.

9. The apparatus of claim 1, further comprising a shaft connected to said handle, wherein at least part of at least one feeder belt is received within said shaft, and wherein said path includes at least two segments within said shaft that are substantially parallel to one another.

10. The apparatus of claim 9, wherein said path within said handle extends further from a longitudinal centerline of said shaft than a radius of said shaft.

11. The apparatus of claim 1, wherein at least one said feeder belt is a continuous loop.

12. A method for operating a surgical apparatus, comprising:
   providing a surgical stapler comprising an end effector, a shaft connected to said end effector, a handle connected to said shaft, and at least one feeder belt extending through said end effector, said shaft and said handle, wherein a plurality of staples are frangibly affixed to each said feeder belt;
   deploying a plurality of said staples from said end effector; and
   advancing at least one said feeder belt along a nonlinear path after said deploying, whereby a plurality of staples are moved into said end effector into position for deployment, and wherein at least part of said nonlinear path moves away from a longitudinal axis of the handle.

13. The method of claim 12, wherein, during said advancing, a portion of said feeder belt moving proximally into said handle from said shaft moves away from a portion of said feeder belt that is moving distally out of said handle into said shaft.

14. The method of claim 12, wherein, during said advancing, a portion of said feeder belt moving distally out of said handle into said shaft moves away from a portion of said feeder belt that is moving proximally into said handle from said shaft.

15. The method of claim 12, wherein, during said advancing, a portion of said feeder belt slides against a mandrel located within said handle.

* * * * *